United States Patent [19]
Lobisch et al.

[11] Patent Number: 5,284,861
[45] Date of Patent: Feb. 8, 1994

[54] PHARMACEUTICAL COMPOSITION COMPRISING FLUPIRTINE AND ITS USE TO COMBAT PARKINSON DISORDERS

[75] Inventors: Michael Lobisch, Ober-Ramstadt; Ralph Venhaus, Heppenheim; Bernd Nickel, Mühltal; Istvan Szelenyi, Schwaig; Jürgen Engel, Alzenau; Peter Emig, Niederdorfelden, all of Fed. Rep. of Germany

[73] Assignee: Asta Medica AG, Fed. Rep. of Germany

[21] Appl. No.: 890,730

[22] Filed: Jun. 1, 1992

Related U.S. Application Data

[62] Division of Ser. No. 726,408, Jul. 10, 1991, Pat. No. 5,162,346.

[30] Foreign Application Priority Data

Jul. 14, 1990 [DE] Fed. Rep. of Germany ....... 4022442

[51] Int. Cl.$^5$ .............................................. A61K 31/44
[52] U.S. Cl. ................................................ 514/356
[58] Field of Search .................................... 514/356

[56] References Cited

U.S. PATENT DOCUMENTS 4,668,684  5/1987  Tibes et al. .......................... 514/277
4,778,799  10/1988 Tibes et al. .......................... 514/277

FOREIGN PATENT DOCUMENTS 0189788  1/1986  European Pat. Off. .
3604575  8/1986  Fed. Rep. of Germany .

OTHER PUBLICATIONS

European Search Report for European Patent No. 91111124 (1992).
Article entitled "Einfluß von Flupirtin, verschiedener . . . ." w/English Translation, pp. 909-911 Aug. 1990 Drug Res. 40 (II) Nr. 8(1990).
Article entitled "Allgemeine pharmakiloqische Untersuchungen . . . . " w/Engl. Transl. Drug-Res. 35(I)Nr. 1(1985) p. 44-45.
One page article Entitled "Flupirtin bei . ." Feb. 28, 1991, p. 28 Pharmazenticle Zeit.136(30)1991 by Jurg Bruggm.
Article entitled "Flupirtin bei chronischen...." by Von R. wurz Fortschr. Med. 109(6) 1991 Feb. 28, pp. 158–160.
Article entitled "Antiparkinsonmittel Pharmakotherapie des . . ." by Forth W., Henschler D. & Rummel V. Edition 5, Allgemeine und Spezielle Pharmakologie und Toxikologie 1987 p. 519–521.
Article entitled "Mode of antinociceptive action of flupirtine in the rat" by Nickel, et al.. The Macmillan Press Ltd. 1989, Br. J. Pharmacol (1989) 97, 835–842.
Book, entitled "Postgraduate Medical Journal" Flupirtine-a centrally acting analgesic 1987, vol. 63, Suppl. 3.

*Primary Examiner*—S. J. Friedman
*Attorney, Agent, or Firm*—Cushman, Darby & Cushman

[57] ABSTRACT

Flupirtine is used for the treatment of disorders involving skeletal muscle tension.

2 Claims, No Drawings

PHARMACEUTICAL COMPOSITION COMPRISING FLUPIRTINE AND ITS USE TO COMBAT PARKINSON DISORDERS

This is a division of application Ser. No. 07/726,408, filed Jul. 10, 1991, now U.S. Pat. No. 5,162,346.

The present invention relates to treatment of skeletal muscle tension disorders with flupirtine and to pharmaceutical compositions containing flupirtine.

BACKGROUND OF THE INVENTION

The pharmaceutically active compound flupirtine (chemical designation 2-amino-3-carbethoxyamino-6-(4-fluorobenzylamino)-pyridine is an analgesic, i.e., it causes an insensibility to pain without anesthesia or loss of consciousness. The preparation of this compound and of its physiologically acceptable salts is described in German patent 1,795,858 and in German patent 3,133,519.

SUMMARY OF THE INVENTION

In accordance with the present invention, it has now been found that flupirtine also has skeletal muscle relaxing effects and is suitable for combating clinical pictures, clinical symptoms and disorders based on muscular tension or a succession of such muscular tensions.

The invention relates to agents for combating disorders and/or clinical symptoms which are based on muscular tension, or a succession of such muscular tensions. Thus, for example, flupirtine displays a good skeletal muscle relaxing effect in addition to the known analgesic effect during continuous measurement of the resistance of the flexor and extensor muscle of the hind leg of the rat. This is shown in the following experimental method:

Experimental method

Female SIV 50-rats, 160 g to 200 g, were used as experimental animals. The animals were kept at room temperatures of 20° C. to 24° C., a relative humidity of 60% to 70% and light-darkness times of 12 to 12 hours. Feed (Atromin ® mature rye) and water were available ad libitum. Flupirtine was used in the form of its maleate.

The muscle relaxing effect was determined by continuously measuring the resistance of the flexor and extensor muscle of the hind legs of the rats. To achieve this, the paw of the right hind leg of the rat was quickly moved up and then down by means of an electronically driven servo motor at 30-second time intervals. The reflex reaction of the rats' flexor and extensor provoked by the compulsory movement of the rat paw, was transmitted to a force transducer and evaluated using a computer (IBM/PC). Parallel to the on-line evaluation, the data were plotted on a conventional plotter and simultaneously recorded on magnetic tape. Before commencement of the experiment the experimental apparatus was calibrated by applying a calibrated 50 gram weight to the force transducer. The animals were then placed in the experimental unit and had 30 minutes' time to adjust thereto. After measuring the initial resistance of flexor and extensor of the rat (control values) flupirtine maleate was applied intraperitoneally and the influence of the compounds on flexor and extensor was recorded, stored and evaluated on-line for 90 minutes, a mean value being calculated every 10 minutes.

The significance of the differences between the mean values of the groups of experimental animals was investigated using Student's T-test.

A muscle-relaxing effect was noted following the intraperitoneal administration of flupirtine in an analgesically effective dose range, no central side effects such as ataxia or reduction in spontaneous motility being observed in the animals treated with flupirtine in the dose range investigated.

For example in the above-mentioned experimental method at a dose of 1 mg/body weight/kg rat, the drug-induced rigidity of the skeletal musculature in the awake rat was reduced by 50%.

The minimum effective dose in the above-described animal experiment is, for example, 1 mg/kg oral 0.1 mg/kg intraperitoneal The general dose range for the effect (animal experiment as above) that may for example be considered is:

1-100 mg/kg oral, in particular 10 to 40 mg/kg 0.1-30 mg/kg intraperitoneal, in particular 1 to 20 mg/kg Flupirtine displays in particular the following differences as compared to other active pharmaceutical compounds with the same direction of action: flupirtine does not cause dependence and has a pronounced analgesic effect.

The muscle relaxing effect of flupirtine also leads to reduction in the rigidity induced in similar manner by reserpine in anti-parkinson agents.

Combination of flupirtine with anti-parkinson agents of this type leads to a superadditive, enhanced skeletal muscle-relaxing effect. Thus, for example, flupirtine also reduces skeletal muscle tone in disorders in which the muscle tone is elevated, e.g. Morbus Parkinson.

The effective doses for this purpose are those already given.

The effect of flupirtine alone and in combination with other known anti-parkinson agents such as (—)-deprenyl, biperiden and L-dopa on reserpine-induced rigidity is set out in the following table.

| Substance | Dose[1] mq/kq i.p. | Decrease in rigidity Flexor % effect | Extensor % effect |
|---|---|---|---|
| Flupirtine | 5 | 53 | 56 |
| (—)—Deprenyl | 1 | 18 | 14 |
| Flupirtine + (—)—Deprenyl | 5 + 1 | 96 | 93 |
| Biperiden | 0.1 | 12 | 16 |
| Flupirtine + Biperiden | 5 + 0.1 | 89 | 96 |
| L-Dopa | 5 | 17 | 11 |
| Flupirtine + L-Dopa | 5 + 5 | 93 | 88 |

[1] i.p. = intraperitoneal

This reduction in rigidity is determined by the previously-described continuous measurement of the resistance of the flexor and extensor muscle at the hind leg of the rat. The only difference in the determination of the rigidity reduction lies in the fact that the animals receive reserpine in a dose of 2.5 mg/kg rat intraperitoneally 16 hours before commencement of the experiment. The reserpine causes the rigidity. The decrease or elimination of this rigidity as a result of flupirtine, various antiparkinson agents and combinations of the latter with flupirtine is then determined as stated.

Indications for which the flupirtine having the new effect in accordance with the invention may be considered are: all disorders which are associated with muscular tension (rigidity) and their sequelae, such as for example neuralgias, arthritis, arthrosis, chronic or episodic tension headache, postoperative disabilities, generalized tendomyopathies, insertion tendopathies, Parkinsonian disorders (in particular the rigidity accompanying Parkinsonian disorders).

Contraindications: Myasthenia gravis.

The pharmaceutical formulations generally contain between 50 mg and 500 mg, preferably 100 mg to 200 mg flupirtine base.

Administration may, for example, be in the form of tablets, capsules, pills, coated tablets, suppositories, ointments, gels, creams, powders, dusting powders, aerosols or in liquid form.

Liquid forms of application that may for example be considered are: oily or alcoholic or aqueous solutions as well as suspensions and emulsions. Preferred forms of application are capsules or tablets containing between 100 mg and 200 mg or solutions containing between 0.1 to 10% by weight of flupirtine.

The individual dosage of flupirtine base may for example lie:

a) in the case of oral medicinal forms between 70 mg and 300 mg, preferably 100 mg to 200 mg, b) in the case of parenteral medicinal forms (for example intravenous, intramuscular) between 8 mg and 80 mg, preferably 10 mg and 100 mg.

(The doses are in each case related to the free flupirtine base)

It is for example possible to recommend 1 to 2 capsules or tablets containing 50 mg to 200 mg of active substance 3 times daily.

Should the flupirtine be used together with anti-parkinson agents in combined manner or form, the weight ratio of flupirtine to the anti-parkinson agent is for example 1 : 0.01 to 1 : 1. In the corresponding products, the flupirtine and anti-parkinson agent are thus for example present in weight ratios of this order.

The acute toxicity of flupirtine in the mouse (expressed by the $LD_{50}$ mg/kg, method after Miller and Tainter: Proc. Soc. Exper. Biol. a. Med. 7 (1944) 261) lies for example in the case of oral application between 600 mg/kg and 800 mg/kg (or above 500 mg/kg).

The invention also for example relates to the following processes to produce a corresponding medicament which contains flupirtine as the main active agent.

a) A process for the preparation of a pharmaceutical composition for combating disorders and symptoms based on muscular tension or which are a consequence of muscular tension, which is characterized that flupirtine or its therapeutically acceptable salts, optionally as well as an anti-parkinson agent, are formulated with conventional pharmaceutical carriers, auxiliary and/or diluting agents into a pharmaceutical composition for the treatment of the above listed disorders.

b) A process for the preparation of an agent for combating disorders and symptoms based on muscular tension or which are a consequence of muscular tension, characterized in that at least flupirtine or a pharmaceutically acceptable salt of flupirtine, optionally as well as an anti-parkinson agent, is mixed together and homogenized respectively with conventional carriers and/or diluents or auxiliary substances at temperatures between 0° and 120° C., preferably 20° and 80° C. and the mixture thereby obtained for the preparation of formulations containing in each dosage unit 50 to 500 mg of flupirtine or a pharmaceutically acceptable salt of flupirtine is poured into hollow cells of appropriate size, or pressed into tablets or filled into capsules of appropriate size or granulated and then pressed into tablets or filled into capsules optionally with addition of additional conventional auxiliary substances.

c) A process for the preparation of an agent for combating disorders and symptoms based on muscular tension or which are a consequence of muscular tension, characterized in that flupirtine or a pharmaceutically acceptable salt of flupirtine, optionally as well as an anti-parkinson agent is mixed with one or several of the following substances: starch, cyclodextrin, urea, cellulose, lactose, formalincasein, modified starch, magnesium stearate, calcium hydrogen phosphate, silica, talcum, phenoxyethanol, the mixture obtained is granulated, optionally with an aqueous solution that contains as a component at least gelatin, starch, polyvinyl pyrrolidone, vinyl pyrrolidonevinyl acetate copolymerizate and/or polyoxyethylene sorbitan monooleate, the granulate is granulated, optionally with one or several of the above mentioned auxiliary substances and this mixture is pressed into tablets or filled into capsules, the tablets or capsules in the dosage unit containing in each case 50 to 500 mg of the active substance flupirtine or the salt thereof.

d) A process for the preparation of an agent for combating disorders and symptoms based on muscular tension or which are a consequence of muscular tension, characterized in that flupirtine or a pharmaceutically salt of flupirtine, optionally as well as an anti-parkinson agent, is suspended and homogenized with one or several of the following auxiliary substances: soya lecitin, oxynex, phenoxyethannol, at temperatures between 31° and 65° C. in molten hard fat or other mixtures containing fatty acid glycerides and the mixture is then poured into hollow cells or filled into capsules, the dosage unit containing 50 to 500 mg of the active flupirtine or a salt thereof.

e) A process for the preparation of an agent for combating disorders and symptoms based o muscular tension or which are a consequence of muscular tension, characterized in that flupirtine or a pharmaceutically acceptable salt of flupirtine, optionally as well as an anti parkinson agent, is homogenized and/or emulsified at a temperature between 20° and 120° C., optionally in the presence of one or several emulsifiers and/or complex formers with at least one of the following substances: water, glycerin, paraffin, Vaseline, aliphatic alcohol with 12 to 25 carbon atoms, aliphatic monocarboxylic acid with 15 to 20 carbon atoms, sorbitan monopalmitate, polyoxyethylene polyol fatty acid ester, single or multivalent low molecular weight aliphatic alcohol, fatty acid glyceride, wax, silicone, polyethylene glycol, silicon dioxide.

f) A process for the preparation of an agent for combating disorders and symptoms based on muscular tension or which are a consequence of muscular tension (solution), characterized in that flupirtine or a pharmaceutically acceptable salt of flupirtine, optionally as well as an antiparkinson agent, is dissolved optionally in the presence of a complex former and/or an emulsifier, at temperatures between 30° and 100° C. in water, physiologically harmless alcohols, polyglycols, polyglycol derivatives, dimethylsulfoxide, triglycerides, partial esters of glycerin, paraffins or oils or mixtures thereof and the solution thereby obtained is optionally made up with so much of the above-named solvents that the final solution, final suspension or final emulsion contains 0.1–10 percent by weight of the active substance flupirtine.

The pharmaceutical compositions or medicaments contain flupirtine or its physiologically acceptable salts as active substance. The active substance is optionally present in a mixture with other pharmacologically or pharmaceutically active substances. The preparation of the pharmaceutical compositions is effected in conventional manner, it also being possible to use conventional and customary pharmaceutical auxiliary substances and other conventional carriers and diluents.

Carrier and auxiliary substances that may for example be considered are those which are recommended or quoted in the following literature references as auxiliary substances for pharmacy, cosmetics and related fields: "Ullmanns Encyklopadie der technischen Chemie", Volume 4 (1953), pages 1 to 39; Journal of Pharmaceutical Sciences, Volume 52 (1963), page 918 et seq.; H.v.Czetsch-Lindenwald, "Hilfsstoffe for Pharmazie und angrenzende Gebiete"; Pharm. Ind. issue 2 (1961), page 72 et seq.; Dr. H. P. Fiedler, "Lexikon der Hilfsstoffe for Pharmazie, Kosmetik und angrenzende Gebiete" Cantor KG, Aulendorf in Württemberg 1981.

Examples thereof are gelatin, natural sugars such as unrefined sugar or lactose, lecithin, pectin, starches (for example corn starch), cyclodextrins and cyclodextrin derivatives/ polyvinyl pyrrolidone, polyvinyl acetate, gelatin, gum arabic, alginic acid, tylose, talcum, lycopodium, silica gel (for example colloidal), cellulose, cellulose derivatives (for example cellulose ether in which the cellulose hydroxy groups are partially etherified with lower saturated aliphatic alcohols and/or lower saturated aliphatic oxyalcohols, for example methyloxypropyl cellulose, methyl cellulose, hydroxypropylmethyl cellulose, hydroxypropylmethyl cellulose phthalate); fatty acids as well as magnesium, calcium or aluminum salts of fatty acids with 12 to 22 carbon atoms, in particular saturated ones (for example stearates), emulsifiers, oils and fats, in particular vegetable fats (for example peanut oil, castor oil, olive oil, sesame oil, cottonseed oil, corn oil, wheat germ oil, sunflower seed oil, cod liver oil, in each case also hydrogenated; mono-, di- and triglycerides of saturated fatty acids $C_{12}H_{24}O_2$ to $C_{18}H_{36}O_2$ and their mixtures, pharmaceutically acceptable single or multivalent alcohols and polyglycols such as polyethylene glycols as well as derivatives thereof, esters of aliphatic saturated or unsaturated fatty acids (2 to 22 carbon atoms, in particular 10–18 carbon atoms) with monovalent aliphatic alcohols (1 to 20 carbon atoms), or multivalent alcohols such as glycols, glycerin, diethylene glycol, pentaerythritol, sorbitol, mannitol and so on, which may optionally also be etherified, esters of citric acid with primary alcohols, acetic acid, benzylbenzoate, dioxolanes, glycerin formals, tetrahydrofurfuryl alcohol, polyglycol ether with $C_1$-$C_{12}$-alcohols, dimethylacetamide, lactamides, lactates, ethyl carbonates, silicons (in particular medium-viscous polydimethylsiloxanes), calcium carbonate, sodium carbonate, calcium phosphate, sodium phosphate, magnesium carbonate and the like.

Other auxiliary substances that may be used are substances which aid disintegration (so called disintegrants) such as: cross-linked polyvinyl pyrrolidone, sodium carboxymethyl starch, sodium carboxymethyl cellulose or microcrystalline cellulose. Known coating substances may also be used. Those that may for example be considered are: polymerizates as well as copolymerizates of acrylic acid and/or methacrylic acid aid/or their esters; copolymerizates of acrylic and methacrylic acid eaters with a low ammonium group content (such as Edragit ® RS), copolymerizates of acrylic and methacrylic acid esters and trimethyl ammonium methacrylate (for example Eudragit ® RL); polyvinylacetate; fats, oils, waxes, fatty alcohols; hydroxypropyl methyl cellulose phthalate or acetate succinate; cellulose-, starch- as well as polyvinylacetate phthalate; carboxymethyl cellulose; methylcellulose phthalate, -succinate, -phthalate succinate and - phthalate-acid half esters; zein; ethyl cellulose as well as -succinate; shellac, gluten; ethylcarboxyethyl cellulose; ethacrylate-maleic acid anhydride copolymer; maleic acid anhydride-vinylmethyl ether copolymer; styrene-maleic acid copolymerizates; 2-ethyl-hexyl-acrylate maleic acid anhydride; crotonic acid-vinyl acetate copolymer; glutamic acid/glutaminic acid ester-copolymer; carboxymethylethyl-cellulose glycerin monooctanoate; cellulose acetate succinate; polyarginine.

Plasticizing agents for coating substances that may be considered are:

Citric and tartaric acid esters (acetyltriethyl-,acetyltributyl-, tributyl-, triethylcitrate); glycerin and glycerin esters (glycerin diacetate, -triacetate, acetylated monoglycerides, castor oil); phthalic acid esters (dibutyl-, diamyl-, diethyl-, dimethyl-, dipropyl-phthalate), D-(2-methoxy or ethoxyethyl)-phthalate, ethylphthalyl-, butylphthalylethyl- and butylglycolate; alcohols (propylene glycol, polyethylene glycols of various chain lengths), adipates (diethyladipate),di-(2-methoxy or ethoxyethyladipate); benzophenone; diethyl- and dibutylsebacate, -succinate, -tartrate; diethylene glycol diproprionate; ethylene glycol-diacetate, -dibutyrate, -dipropionate; tributylphosphate, tributyrin; polyethyleneglycol sobitan monooleate (polysorbates such as polysorbate 80); sorbitan monooleate.

For the manufacture of solutions or suspensions it is for example possible to use water or physiologically acceptable organic solvents, such as for example ethanol, propanol, isopropanol, 1,2-propylene glycol, polyglycols and their derivatives, dimethylsulfoxide, fatty alcohols, triglycerides, partial esters of glycerin, paraffins and the like.

For injectable solutions or suspensions it is for example possible to use non-toxic parenterally acceptable diluents or solvents, such as for example: water, 1,3-butanediol, ethanol, 1,2-propylene glycol, polyglycols in mixture with water, Ringer's solution, isotonic salt solution or also solidified oils including synthetic mono- or diglycerides or fatty acids such as oleic acid.

In the manufacture of the formulations it is for example possible to use known and conventional solubilizers or emulsifiers. Solubilizers and emulsifiers which may for example be used are: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters or sorbitan, polyoxyethylated fats, polyoxyethylated oleotriglycerides, linolizated oleotriglycerides, polyethyleneoxide condensation products of fatty alcohols, alkylphenols or fatty acids or also 1-methyl-3-(2-hydroxyethyl)-imidazolidone-(2). In this case polyoxyethylated means that the substances in question contain polyoxyethylene chains, the degree of polymerization of which generally lies between 2 and 40 and in particular between 10 and 20.

Polyoxyethylated substances of this kind may for example be obtained through reaction of hydroxyl group-containing compounds (for example mono- or diglycerides or unsaturated compounds such as those containing oleic acid residues) with ethylene oxide (for example 40 mol ethylene oxide per mol glyceride).

Examples of oleotriglycerides are olive oil, peanut oil, castor oil, sesame oil, cottonseed oil, corn oil. See also Dr. H. P. Fiedler "Lexikon der Hilfsstoffe for Pharmazie, Kosmetik und angrenzende Gebiete" 1971, pages In addition, it is also possible to add preservatives, stabilizers, buffer substances for example calcium hydrogen phosphate, colloidal aluminum hydroxide, flavor correcting substances, sweeteners, colorants, antioxidants and complex formers for example ethylene diamine-tetra-acetic acid) and the like. Adjustment to a pH range of ca. 3 to 7 is optionally possible using physiologically acceptable acids or buffers to stabilize the molecule of active substance. In general a neutral to weakly acidic (up to pH 5) pH value is preferred.

For the preparation of topical (dermally applied) formulations, it is possible to use the above mentioned substances and spreadable or liquid hydrocarbons such as Vaseline or paraffin or gels of paraffin hydrocarbons and polyethylene, fats and oils of plant or animal origin which may in part also be hydrated or synthetic fats such as glycerides of the $C_8$–$C_{18}$ fatty acids, as well as beeswax, cetylpalmitate, wool wax, wool wax alcohols; fatty alcohols such as cetyl alcohol, stearyl alcohol, polyethylene glycols of molecular weight 200 to 20,000; liquid waxes such as isopropylmyristate, isopropylstearate, ethyloleate; emulsifiers such as sodium, potassium and ammonium salts of the stearic acids or palmitic acids as well as triethanolamine stearate, alkali salts of the oleic acids, ricinic acid, salts of sulfurated fatty alcohols such as sodium lauryl sulphate, sodium acetyl sulphate, sodium stearyl sulphate, salts of gallic acid, sterols such as cholesterol, partial fatty acid esters of multivalent alcohols such as ethylene glycol monostearate, glycerol monostearate, pentaerythritol monostearate, partial fatty acid esters of sorbitan, partial fatty acid esters of polyoxyethylene sorbitan, sorbitol ethers of polyoxyethylene, fatty acid esters of polyoxyethylene, fatty alcohol ethers of polyoxyethylene, fatty acid esters of saccharose, fatty acid esters of polyglycerol, lecithin.

Antioxidants that may for example be considered are sodium metabisulphite, ascorbic acid, gallic acid, gallic acid alkyl ester, butylhydroxyanisole, nordihydroguaiaretic acid, tocopherols as well as tocopherols + synergists (substances which bind heavy metals through complex formation, for example lecithin, ascorbic acid, phosphoric acid). The addition of synergists substantially enhances the antioxidant effect of the tocopherols. The conserving agents that may for example be considered are sorbic acid, p-hydroxybenzoic acid esters (for example lower alkyl esters), benzoic acid, sodium benzoate, trichloroisobutylalcohol, phenol, cresol, benzethonium chloride and formalin derivatives.

The pharmaceutical and galenic treatment of the compounds of the invention is effected according to the conventional standard methods. For example, active substance(s) and auxiliary and/or carrier substances are well mixed by means of stirring or homogenizing (for example using conventional mixing devices), working generally taking place at temperatures between 20° and 80° C., preferably 20° to 50° C., particularly at room temperature. In this connection reference is also made to the following standard work: Sucker, Fuchs, Speiser, "Pharmazeutische Technologie", publishers: Thieme-Verlag Stuttgart, 1978.

Application may be to the skin or mucous membrane or to the inside of the body, for example oral, enteral, pulmonal, rectal, nasal, vaginal, linnual, intravenous, intraarterial, intracardial, intramuscular, intraperitoneal, intracutaneous or subcutaneous. The parenteral forms of preparation are in particular sterile or sterilized preparations.

DETAILED DESCRIPTION OF PREFERRED EMBODIMENTS

The invention is illustrated by the following examples:

Tablets:

10 kg 2-amino-3-carbethoxyamino-6-(4-fluorobenzylamino)-pyridine maleate are mixed with 2.5 kg calcium hydrogen phosphate and 2.5 kg corn starch and the mixture is granulated with a solution of 1 kg polyvinyl pyrrolidone in 4 kg demineralized water in conventional manner. After the addition of 1.3 kg corn starch, 2 kg microcrystalline cellulose, 0.6 kg magnesium stearate and 0.1 kg highly disperse silicon dioxide, tablets are pressed weighing 200 mg having a diameter of 9 mm and a radius of curvature of 10 mm with score indentation. The breaking strength of the tablets is 80N to 100N (Schleuniger breaking strength tester). The disintegration time according to DAB 8 is 5 minutes. Each capsule contains 100 mg of active substance.

Capsules

A capsule filling is prepared in an analogous manner to the above described method of manufacture for tablets which is filled into hard gelatin capsules of the appropriate size. Filling amount per capsule: 200 mg. Each capsule contains 100 mg active substance. Oily suspension containing 15% flupirtine maleate:

32.5 g highly disperse, amorphous, hydrophobic silicon dioxide (trade name: Aerosil ® 972/Degussa), 0.5 g micronized saccharin sodium, 1.5 g fine ground sodium cyclamate, 0.1 g iron oxide, red, 0.5 g strawberry flavor, 75 g flupirtine maleate and 0.375 g Oxynex LM (E. Merck/Darmstadt) are homogenously suspended in 400 g medium chain-length triglycerides (trade name: Miglylol 812/Hls Troisdorf). The suspension is made up to 500 g with medium chain triglycerides and mixed.

Each gram of suspension contains 150 mg flupirtine.

Injection solution

The manufacturing method applies to a batch of 20 liters (=6500 ampoules):

Manufacturing method:

1. 10.0 liters of water are heated to 70° C. and the solution is left to stand for one hour at 70° C. after addition of 1562.0 g gluconic acid delta lactone. The solution is gassed with nitrogen during this process.

2. 8000.0 g polyethylene glycol of molecular weight 380 to 420 are weighed into solution 1 and the solution is heated to 70° C. with nitrogen gassing.

3. 30.0 g of sodium disulfite are dissolved in 500.0 ml of water gassed with nitrogen.

4. Solution 3 is added to solution 2.

5. 666.6 g flupirtine base are sieved through a sieve of mesh size 0.3 mm and dissolved in solution 4 with intensive nitrogen gassing.

6. Solution 5 is cooled and made up to 20 liters with nitrogen-gassed water.

7. Solution 6 is sterile filtered through a membrane filter of pore size 0.2 μm with a glass fiber pre-filter.

8. In-process check: measurement of the oxygen content of solution 7 using oxygen electrode. Measurement of the pH value of solution 7.

9. Solution 7 is filled under aseptic conditions and under nitrogen gassing into colorless 3 ml ampoules. Each ampoule contains 164.5 mg flupirtine gluconate in 3 ml solution.

What is claimed is:

1. A pharmaceutical composition comprising an effective amount of flupirtine and a compound effective for the treatment of parkinson disorders as indicated by the reserpine-induced rigidity test, the ratio of flupirtine to said compound effective for the treatment of parkinson disorders being in the range 1:0.01 to 1:1.

2. A pharmaceutical composition as set forth in claim 1 in which said compound effective for the treatment of parkinson disorders is selected from the group consisting of L-dopa, (−)-deprenyl and biperiden.

* * * * *